(12) United States Patent
Bouwens et al.

(10) Patent No.: US 7,604,991 B2
(45) Date of Patent: Oct. 20, 2009

(54) METHOD OF GENERATING ISLET BETA-CELLS FROM EXOCRINE PANCREATIC CELLS

(75) Inventors: Luc Bouwens, Dworp (BE); Luc Baeyens, Buggenhout (BE)

(73) Assignees: Vrije Universiteit Brussel, Brussels (BE); Opus NV, Borchtlombeek (BE)

( * ) Notice: Subject to any disclaimer, the term of this patent is extended or adjusted under 35 U.S.C. 154(b) by 131 days.

(21) Appl. No.: 10/561,449

(22) PCT Filed: Jun. 21, 2004

(86) PCT No.: PCT/BE2004/000089

§ 371 (c)(1),
(2), (4) Date: Nov. 22, 2006

(87) PCT Pub. No.: WO2004/113512

PCT Pub. Date: Dec. 29, 2004

(65) Prior Publication Data

US 2007/0292388 A1    Dec. 20, 2007

(30) Foreign Application Priority Data

Jun. 20, 2003    (EP)    ................... 03447164

(51) Int. Cl.
C12N 5/00    (2006.01)
C12N 5/06    (2006.01)
C12N 5/08    (2006.01)
(52) U.S. Cl. ..................... 435/377; 435/325
(58) Field of Classification Search ............ None
See application file for complete search history.

(56) References Cited

U.S. PATENT DOCUMENTS 6,815,203 B1 * 11/2004 Bonner-Weir et al. ....... 435/377
2002/0155598 A1    10/2002 Kerr-Conte et al.
2006/0122104 A1 *  6/2006 Presnell et al. ................. 514/12

FOREIGN PATENT DOCUMENTS

WO    WO 01/32839 A2    5/2001

OTHER PUBLICATIONS

European Search Report dated Nov. 16, 2007 relating to European Application EP 04 73 7673.
Ramiya K. Vijayakumakumar et al. "Reversal of insulin-dependent diabetes using islets generated in vitro from pancreatic stem cells", *Nature Medicine, Nature America*, vol. 6, No. 3, Mar. 2000 pp. 278-282, XP000864764.
Hirosato Mashima et al., "Betacellulin and Activin A Coordinately Convert Amylase-secreting Pancreatic AR42J Cells into insulin-secreting Cells", *Journal of Clinical Investigation*, vol.97, No. 7, Apr. 1, 1996, pp. 1647-1657, XP000670303.
Ki-Ho Song et al., "In vitro transdifferentiation of adult pancreatic acinar cells into insulin-expressing cells", *Biochemical and Biophysical Research Communications*, vol. 316, No. 4, Apr. 16, 2004, pp. 1094-1100, XP004496901.
Yelena Guz et al., "Regeneration of Pancreatic β Cells from Intra-Islet Precursor Cells in an Experimental Model of Diabetes", *Endocrinology*, vol. 142, No. 11, Nov. 2001, pp. 4956-4968, (available at http://www.endo.endojournals.org).
I. Rooman et al., Modulation of rat pancreatic acinoductal transdifferentiation and expression of PDX-1 in vitro, *Diabetologia*, Springer-Velag 2000, vol. 43, pp. 907-914.
Ilse Rooman et al., "Mitogenic Effect of Gastrin and Expression of Gastrin Receptors in Duct-like Cells of Rat Pancreas", *Gastroenterology*, vol. 123, 2001, pp. 940-949.
Ilse Rooman et al., Gastrin Stimulates β Cell Neogenesis and Increases Islet Mass From Transdifferentiated but Not From Normal Exocrine Pancreas Tissue, *Diabetes*, vol. 51, Mar. 2002, pp. 686-690.
Danling Gu et al., "Endocrine/Exocrine Intermediate Cells in Streptozolocin-Treated INS-IFN-γ Transgenic Mice", *Biomedische Bibl*, vol. 15, No. 3, 1997, pp. 246-250.
Yuehua Jiang et al., "Pluripotency of mesenchymal stem cells derived from adult marrow", *Nature*, vol. 418, Jul. 2002, pp. 41-49.
Corentin Cras-Méneur et al., "Epidermal Growth Factor Increases Undifferentiated Pancreatic Embryonic Cells In Vitro: A Balance Between Proliferation and Differentiation", *Diabetes*, vol. 50, Jul. 2001, pp. 1571-1579.
Päivi J. Miettinan et al., "Impaired migration and delayed differentiation of pancreatic islet cells in mice lacking EGF-receptors", *Development*, vol. 127, 2000, pp. 2617-2627.
Koji Yamamoto et al., "Recombinant Human Betacellulin Promotes the Neogenesis of β-Cells and Ameliorates Glucose Intolerance in Mice With Diabetes Induced by Selective Alloxan Perfusion", *Diabetes*, vol. 40, Dec. 2000, pp. 2021-2027.
Eugenio Bertelli et al., "Intermediate endocrine-acinar pancreatic cells in duct ligation conditions", *American Physiological Society*, vol. 273, 1997, pp. 1641-1649.
Susan Bonner-Weir et al., In vitro cultivation of human islets from expanded ductal tissue, *PNAS*, vol. 97, No. 14, Jul. 5, 2000, pp. 7999-8004.
Luc Bowens, "Transdifferentiation Versus Stem Cell Hypothesis for the Regeneration of Islet Beta-Cells in the Pancreas", *Microscopy Research And Technique*, vol. 43, 1998, pp. 332-336.
Luc Bowens et al., "Islet cell neogenesis in the pancreas", *Biomedische-Bibl*, 1996, vol. 427, pp. 553-560.

(Continued)

*Primary Examiner*—Daniel C Gamett
(74) *Attorney, Agent, or Firm*—Bacon & Thomas, PLLC (57) ABSTRACT

The present invention discloses an in vitro method wherein mammalian beta-cell differentiation can be induced in dedifferentiated exocrine pancreatic cells in a medium comprising ligands of the EGF receptor and the GP130 receptor, such as EGF and LIF. Insulin secreting cells, obtainable by this method, provide a means for the treatment of diabetes by islet transplantation.

12 Claims, 3 Drawing Sheets

OTHER PUBLICATIONS

Stephen J. Brand et al., "Pharmacological Treatment of Chronic diabetes by Stimulating Pancreatic β-Cell Regeneration with Systemic Co-administration of EGF and Gastrin", *Pharmaeology & Toxicology*, vol. 91, 2000, pp. 414-420.

Jean Buteau et al., "Glucagon-Like Peptide 1 Induces Pancreatic β-Cell Proliferation Via Transactivation of t he Epidermal Growth Factor Receptor", *Diabetes*, vol. 52, Jan. 2003, pp. 124-132.

Daniel C. Drucker, "Glucagon-Like Peptides: Regulators of Cell Proliferation, Differentiation, and Apoptosis", *Molecular Endocrinology*, vol. 17, No. 2, 2003, pp. 151-171.

Helena Edlund, "Pancreatic Organogenesis—Developmental Mechanisms and Implications for Therapy", *Reviews*, vol. 3, Jul. 2002, pp. 524-532.

Viti Jane et al: "Epidermal Growth Factor Receptors Control Competence to Interpret Leukemia Inhibitory Factor as an Astrocyte Inducer in Developing Corex." The Journal of Neuroscience: The Official Journal of the Society for Neuroscience. Apr. 15, 2003, vol. 23, No. 8, Apr. 15, 2003, pp. 3385-3393, XP002299605.

* cited by examiner

METHOD OF GENERATING ISLET BETA-CELLS FROM EXOCRINE PANCREATIC CELLS

FIELD OF THE INVENTION

The present invention relates to methods of differentiating pancreatic cells. The present invention further relates to insulin secreting cell populations for the treatment of diabetes.

BACKGROUND OF THE INVENTION

Understanding the regulation of beta-cell neogenesis in the pancreas could lead to applications in the field of cell replacement or regeneration therapies for diabetes [Yamaoka T. in *Biochem Biophys Res Commun.* (2002) 296, 1039-43]. For instance, islet transplantation can restore the functional beta-cell mass in diabetes patients [Shapiro et al in *N Engl J Med.* (2000)343, 230-238], but it is seriously hampered by the shortage in donor tissue. This problem could be solved by finding ways of generating more islet cells from the available pancreatic tissue, by the process of neogenesis [Bouwens & Kloppel in *Virchows Arch.* (1996) 427, 553-560]. Despite a lot of progress in the understanding of pancreas development during the last decade, the extracellular factors that specify islet cell differentiation in the embryo remain unknown [Edlund in *Nat Rev Genet.* (2002) 3, 524-532]. In adult mammals, the endocrine pancreas can expand or regenerate under certain experimental conditions, mainly as a result of islet cell neogenesis from progenitor cells [Bouwens & Kloppel cited supra]. The exact nature of the latter remains elusive while duct cells, acinar cells, or intraislet cells have been suggested bear progenitor capacity [Bouwens & Kloppel in *Virchows Arch.* (1996) 427, 553-560; Edlund in *Nat Rev Genet.* (2002) 3, 524-532; Bouwens in *Microscopy Research and Technique* (1998) 43, 332-336; Guz et al. in *Endocrinology.* (2001) 142, 4956-4968; Bonner-Weir et al. in *Proc Natl Acad Sci USA.* (2000) 97, 7999-8004; Ramiya V K et al. *Nat Med.* (2000) 6, 278-282].

It is difficult to draw firm conclusions from whole pancreas studies both with respect to cell derivation and to the specific regulatory factors. Therefore, in vitro models are preferred to study islet neogenesis starting from defined cell preparations isolated from the pancreas. Very few in vitro studies have been able to demonstrate the feasibility of inducing islet neogenesis from adult tissue. It has already been reported that additional islet cells could be generated from monolayer cultures of adult pancreatic tissue. Confirmation of these findings, in order to unravel the nature of the progenitor cells, of the regulatory factors, and to improve the efficacy of generating islet cells is still lacking.

Human pancreatic derived cell cultures that were treated with KGF (keratinocyte growth factor) and nicotinamide, resulted in increases in insulin content after 3 to 4 weeks. Also, cystic structures containing islet cells budded from the monolayer under influence of extracellular matrix [Bonner-Weir et al. cited supra]. The precursors responsible for this neogenesis were characterised as cells expressing the ductal marker cytokeratin-19 [Gao et al. cited supra]. In another study, long-term cultures were obtained from diabetic NOD mouse pancreas under glucose-free conditions, and these could be stimulated to generate islet-like structures in the presence of glucose [Ramiya V K et al. in *Nat Med.* (2000) 6, 278-282]. These cells did not reach functional maturity in vitro. It is at present unclear whether the latter observations may have been due to "passenger" stem cells derived from the blood circulation, which have been discovered recently in NOD mice [Kodama et al. in *Science* (2003) 302, 1223-1227].

Differentiated exocrine cells can revert to a partially dedifferentiated state thereby re-acquiring embryonic plasticity [Bouwens & Kloppel in *Virchows Arch.* (1996) 427, 553-560; Rooman et al. in *Diabetologia* 43, 907-914 (2000); Rooman et al. in *Gastroenterology* 121, 940-949 (2001); Rooman et al. in *Diabetes* 51, 686-690, (2002)]. This indicated that exocrine cells, the great majority of cells in this organ, can be brought to transdifferentiate into endocrine cells under the appropriate conditions.

Exocrine acinar cells can transdifferentiate into endocrine beta-cells [Bouwens in *Microscopy Research and Technique* (1998) 43, 332-336] and there have been indications from in vivo studies for the existence of acinar-islet transitional cells [Gu et al. in *Pancreas* (1997) 15, 246-2501; Bertelli E, Bendayan M in *Am J Physiol* (1997) 273, C1641-C1649]. Since acinar cells can lose amylase and gain ductal characteristics [Rooman et al. (2000) & (2001) cited supra] the appearance of transitional cells co-expressing ductal markers like cytokeratin and insulin [Wang et al. in *Diabetologia.* (1995) 38, 1405-1411] could also represent cells that were initially derived from acinar cells. It has been demonstrated that the amylase-secreting cell line AR42J, derived from an acinar tumor, can transdifferentiate into the beta-cell phenotype in vitro [Mashima et al. in *J Clin Invest.* (1996) 97, 1647-1654]. The present invention reports the in vitro transdifferentiation of acinar cells into beta-cells in a primary culture model with a specific combination of growth factors.

LIF (Leukemia Inhibitory Factor) is a pleiotropic cytokine for which a function in pancreatic development has so far not been described. It is a well-known regulator of stem cell proliferation and differentiation and is widely used to prevent differentiation of embryonic stem cells. Recently, it was reported to stimulate the proliferation of multipotent adult progenitor cells (without differentiation of the cells) in combination with EGF and PDGF [Jiang et al. in *Nature* (2002) 418, 41-49].

EGF (Epidermal Growth Factor) and other EGF-family members have been implicated in the regulation of embryonic development as well as regeneration of the endocrine pancreas. EGF stimulates proliferation of the undifferentiated pancreatic precursor cells in vitro [Cras-Meneur et al. in *Diabetes.* (2001) 50, 1571-1579]. In transgenic mice lacking functional EGF-receptors, islet morphogenesis is impaired and beta-cell differentiation is delayed [Miettinen et al. in *Development* (2000) 127, 2617-2627]. Betacellulin, a growth factor which also operates via the EGF-receptor, was found to promote islet regeneration in subtotally pancreatectomized rats (25Ii) and in alloxan-diabetic mice [Yamamoto et al. in *Diabetes.* (2000) 49, 2021-2027]. Glp-1, another factor that stimulates beta-cell neogenesis [Drucker in *Mol Endocrinol.* (2003) 17, 161-171] has also been shown to transactivate the EGF-receptor [Buteau et al. in *Diabetes.* (2003) 52, 124-132]. In combination with gastrin hormone, EGF was shown to stimulate beta-cell regeneration in streptozotocin-diabetic rats [Brand et al. in *Pharmacol Toxicol.* (2002) 91, 414-420].

LIF and EGF have been reported to act synergistically as signals that regulate the differentiation of neurons and glial cells in embryos [Viti et al. in *J. Neurosci.* (2003) 15, 3385-3393]. In astrocyte progenitors EGF increases the competence to interpret LIF as an astrocyte-inducing signal via increased STAT3 phosphorylation. LIF is also considered a key signal for injury-induced neurogenesis in the adult [Bauer et al. in *J. Neurosci.* (2003) 23, 1792-1803].

SUMMARY OF THE INVENTION

According to one aspect the present invention relates to an in vitro method of generating insulin producing beta cells from a population comprising or consisting of dedifferentiated exocrine pancreatic cells of a first mammal, said method comprising the steps of: a) providing said population of dedifferentiated exocrine pancreatic cells in a culture medium, b) adding one or more ligands of the gp130 receptor of a second mammal and/or adding ligands of the EGF receptor of a third mammal to said culture medium, c) incubating said dedifferentiated exocrine pancreatic cells in said culture medium comprising said one or more ligands of the gp130 receptor and/or said one or more ligands of the EGF receptor.

In one embodiment the method is performed by adding in step b) one or more ligands of the gp130 receptor of a second mammal without adding one ore more ligands of the EGF receptor of a third mammal to said culture medium, In a particular embodiment the method is performed by adding in step b) both one or more ligands of the gp130 receptor of a second mammal as well as adding one or more ligands of the EGF receptor of a third mammal to said culture medium, According to one embodiment, the ligand of said gp130 receptor is LIF, such as human or humanised LIF. According to one embodiment LIF is added to the culture medium in a concentration between 10 and 100 ng/ml, or between 10 and 25 ng/ml or between 100 and 500 ng/ml. According to one embodiment the ligand of said EGF receptor is a human or humanised ligand of said EGF receptor. According to another embodiment the ligand of said EGF receptor is EGF such as human or humanised EGF. According to one embodiment EGF is added to the culture medium in a concentration between 10 and 100 ng/ml or between 10 and 25 ng/ml or between 100 and 500 ng/ml. Generally, the one or more ligands of the gp130 receptor and/or one or more of the ligands of the EGF receptor are added to the culture medium in a concentration between 1 and 10 000 ng/ml. According to a particular embodiment, the method further comprises the step of adding bFGF (basic fibroblast growth factors) to said culture medium during step b. According to a particular embodiment the medium is free from KGF (keratinocyte growth factor) or a gastrin/CCK receptor ligand. In particular embodiments the incubation step in the present method is performed during 7, 6, 5 or even less than 5 days namely 4 or 3 days. The population of dedifferentiated exocrine pancreatic cells which can be used, for the method of the invention is according to one embodiment selected from the group consisting of duct cells, acinar cells and islet cells. Also mixtures of these types cells, or also cell populations, comprising a certain ratio of one or more of the cells types consisting of the group consisting of duct cells, acinar cells and islet cells can be used in the present invention. According to another embodiment, an additional step prior to step a) is performed wherein beta cells are depleted. According to another embodiment, in order to reduce the growth of fibroblast cells, dedifferentiation and redifferentiation is performed in the presence of genitimycine. Cells which can be used according to the methods of the present invention are all types of mammalian cells including rodent, porcine, monkey and human cells. In a particular embodiment, the mammalian cells are rat cells, the one or more ligands of said EGF receptor comprise human EGF the one or more ligands of gp130 receptor comprise murine LIF.

Another aspect of the invention relates to a population of mammalian pancreatic cells comprising mammalian insulin producing beta cells obtainable by any of the here above describes embodiments of the method of the present invention. In one embodiment, this population of mammalian pancreatic cells comprises from about 5 to about 15 percent of insulin-positive cells. In another embodiment, this population of mammalian pancreatic cells, after exposure to conditions such as to 20 mM glucose for 4 hours at 37° C. in RPMI-1640 medium supplemented with 10% fetal bovine serum shows a more than 2 fold increase in insulin secretion when compared to the insulin secretion prior to said exposure to glucose.

In another embodiment, this population of mammalian pancreatic cells are able to provide an insulin secretion of at least 10 ng/ml after exposure of said population to conditions such as 20 mM glucose for 4 hours at 37° C. in RPMI-1640 medium supplemented with 10% fetal bovine.

Another aspect of the invention relates to a population of cells comprising mammalian insulin producing beta cells wherein said cell population comprises cells having at least one feature of a differentiated beta cell and at least one feature of an undifferentiated beta cell in the same individual cell. A feature of a differentiated beta cell can be for example insulin secretion and a feature of an undifferentiated beta cell can be CK20 expression and/or binuclearity. The present invention also relates to such a population of mammalian pancreatic cells which is obtainable by any of the embodiments of the above described redifferentation method.

Another aspect of the present invention relates to a population of mammalian pancreatic cells comprising mammalian insulin secreting beta cells wherein said cell population comprises a first subpopulation of cells having markers of undifferentiated or dedifferentiated cells and comprises a second subpopulation of cells having markers of differentiated cells. Markers of differentiated cells are for example C-peptide-I, Pdx-1, Glut-2 or insulin. Markers of dedifferentiated or undifferentiated cells are for example cytokeratin 7, cytokeratin 19, cytokeratin 20, CCKB receptor for gastrin, PGP9.5 or notch-1 receptor. The present invention also relates to such a population of mammalian pancreatic cells which is obtainable by any of the embodiments of the above described redifferentation method.

In another aspect, the present invention relates to a pharmaceutical composition comprising a therapeutically active amount of a mammalian pancreatic cell population comprising redifferentiated cells which are obtainable by the method of the present invention.

In another aspect, the present invention relates the use of a mammalian pancreatic cell population comprising redifferentiated cells which are obtainable by the method of the present invention for the manufacture of a medicament. In a particular embodiment, the medicament is used for the treatment of diabetes type 1 or type 2.

In yet another aspect, the present invention relates to a method for the treatment of diabetes type 1 or type 2 comprising the step of administering an effective amount of the pharmaceutical composition comprising a therapeutically active amount of a mammalian pancreatic cell population comprising redifferentiated cells which are obtainable by the cultivation methods of the present invention In yet another aspect, the present invention relates to the use of a combination of a human or humanised ligand of a EGF receptor, and a human or humanised ligand of the gp130 receptor for the preparation of a medicament. In one embodiment the medicament is used for the treatment of diabetes type 1 or type 2. In another embodiment the human or humanised ligand of a EGF receptor is human EGF and the human or humanised ligand of the human gp130 receptor is human LIF.

In yet another aspect the present invention relates to the use of a human or humanised ligand of the gp130 receptor for the preparation of a medicament for the treatment of diabetes type 1 or type 2. In one embodiment the human or humanised ligand of the gp130 receptor is LIF.

In yet another embodiment the invention relates to an in vitro method for determining the degree of redifferentiation of dedifferentiated mammalian pancreatic cells comprising the steps of determining one or more parameters selected from the group consisting of a) The presence of CK20, CK7 or CK 19, b) the ocurrence of binucleated cells, c) the presence of insulin positive cells, d) the presence of C-peptide, Pdx-1 and Glut-2, e) the presence of gastrin CCKB receptor, PGP9.5 and notch-1 receptor on said mammalian pancreatic cells. The invention also relates to a population of mammalian pancreatic cells being identifiably by this in vitro method for determining the degree of redifferentiation of dedifferentiated The present invention relates to a method of generating in vitro insulin producing mammalian beta cells from dedifferentiated pancreatic cells. In one embodiment this is done by incubating said dedifferentiated pancreatic cells in a medium comprising a ligand of the EGF receptor, for example EGF or TGF-alpha. Optionally, the medium further comprises a ligand of the gp130 receptor such as LIF. As an alternative the medium optionally comprises bFGF. The dedifferentiated pancreatic cells used in this method are for example duct cells, acinar cells or islet cells. These dedifferentiated cells can be depleted from beta cells prior to the incubation into this medium. The dedifferentiated pancreatic cells are mammalian cells obtained, for example, from rodents (rat, mouse), cattle, pigs and primates including humans.

In another aspect, the present invention relates to a population of insulin producing cells obtainable from dedifferentiated pancreatic cells by the above described method. Such a population of insulin producing cells shows preferably an at least 2 fold increase in insulin secretion when exposed to glucose (e.g. 20 mM glucose for 4 hours). The population of cells can be further characterised by their immunoreactivity for markers such as C-peptide-I, Pdx-1 and Glut-2. They can also in addition be characterised by the presence of less than 10% cytokeratin positive cells and/or less than 7% binuclear cells.

The invention relates in a further aspect to a pharmaceutical composition comprising a cell population of insulin producing cells obtainable from dedifferentiated pancreatic cells by the method of the present invention, further comprising at least one pharmaceutically acceptable carrier. A cell population of insulin producing cells obtainable from dedifferentiated pancreatic cells by the method of the present invention can be used for the manufacture of a medicament for the treatment of diabetes type 1 or type 2. Thus, the invention also relates to a method for the treatment of diabetes comprising the step of administering the pharmaceutical composition of the present invention to an individual in need of it.

In another aspect, the invention relates to the use of a ligand of the EGF receptor (e.g. EGF) or a ligand of the gp130 receptor (e.g. LIF) for the preparation of a medicament for the treatment of diabetes, in order to increase in vivo the amount of insulin secreting beta cell population.

As indicated above, application of islet transplantation as a treatment for diabetes is hampered by an inadequate supply of insulin-producing cells. In the present invention insulin-producing beta cells are generated from exocrine cells, which represent the great majority of cells in the pancreas, e.g. in humans and other mammals.

The present invention provides a method wherein beta-cell neogenesis can be induced from exocrine cells by the combination of two soluble factors in the medium, namely EGF and LIF. The invention provides an important advancement in the treatment of diabetes by islet transplantation, by providing a way to overcome the problem of insufficient donor beta-cells.

When applied to human cells, the present invention provides an important advancement in the treatment of diabetes by islet transplantation, by providing a way to overcome the problem of insufficient donor beta-cells.

DETAILED DESCRIPTION OF THE INVENTION

"added", "adding" or "addition" in the present invention refers to compounds EGF receptor and Gp130 receptor ligands, such as LIF and EGF, which are supplemented separately to the medium. It does not refer to unknown levels of compounds which are present in the medium due to secretion by the cells. It also does not refer to low amounts of compounds which are present in serum which is added to a basal growth medium. Concentrations of added compounds in the medium are in the ng/ml range and may vary from about 1, 10, 25, 50, 100, 250, 500, up to 1000 ng/ml. In a specific embodiment the concentration of added compounds for each compound separately varies between 10 and 100 ng/ml. In another specific embodiment the concentration of added compounds for each compound separately varies between 20 and 100 ng/ml.

"Dedifferentiated exocrine pancreatic cells" refers to those cells which are to a lesser or greater extent dedifferentiated and have re-acquired embryonic plasticity. Typical features of differentiated cells which have been lost by the differentiated cells are the expression of amylase and other zymogens, such as pancreatic trypsinogen, trypsin and lipase, the insulin-transactivating transcription factor Pdx-1, the beta-cell specific glucose transporter Glut-2, and the C-peptide-I component of unprocessed proinsulin. Typical features of the embryonic plasticity which have been acquired by the dedifferentiated cells are the expression of cytokeratins 7, 19 and/or 20. In addition there can be expression of the cholecystokinin B CCKB-receptors for gastrin, the neuroendocrine markers PGP9.5 (neuron-specific ubiquitin c-terminal hydrolase) and the Notch-1 receptor. Typical pancreatic cell types which can be dedifferentiated according to the present invention are acinar cells, duct cells and non-endocrine islet cells.

"Beta cells" are generally known as specialized cells found in clusters (islets) in the pancreas. Beta cells regulate glucose levels in the bloodstream by making insulin, monitoring glucose levels, and secreting insulin in response to elevated glucose levels. Together with glucagon secreting alpha cells, they form the majority of the endocrine cell population of the pancreas.

The islets or islet of Langerhans are special groups of cells in the pancreas. They make and secrete hormones that help the body break down and use food. These cells sit in clusters in the pancreas. There are five types of cells in an islet: beta cells, alpha cells, delta cells, which make somatostaton, and PP cells and D1 cells.

The present invention makes use of the exocrine fraction which is normally discarded after isolation of islets of Langerhans from the pancreas of humans and other mammals. In certain embodiments pancreatic exocrine cells are derived from adult, postnatal or prenatal pancreas. In a certain embodiment, the redifferentiated endocrine pancreatic cells are used for transplantation into a different species. In another embodiment redifferentiated endocrine cells are used for transplantation into a different individual of the same species. In yet another embodiment cells, exocrine pancreatic cells are obtained from an individual and the redifferentiated endocrine cells are used for transplantation into the same individual. Dedifferentiated cells can be maintained in culture for longer periods up to 14 days. Alternatively, the dedifferentiated cells are frozen and stored.

The present invention relates to the use of EGF (epidermal growth factor) which binds to the EGF receptor (EGFR) and activates a downstream pathway. Consequently truncated or mutated versions of EGF which retain the activity of binding and activating the EGF receptor can be used as an alternative for the methods of the present invention. Within the same context, ligands such as EGF from other animal species than the species from which the pancreatic cells are isolated can be used if the bind and activate the receptor. For these purposes the sequence of such a ligand from one species can be modified in order to acquire the desired binding and activation properties on the cell population obtained from another species. For in vivo purposes a ligand from a non-human mammal can be "humanised" in order to acquire activity within a human and to avoid an immune response by the human immune system. Equally, other naturally or modified proteins which are a ligand for EGFR can be used for the methods of the present invention. Examples hereof are Transforming Growth Factor-alpha, amphiregulin, betacellulin and PoxVirus Growth Factor).

The present invention relates to the use of LIF (Leukemia inhibitory factor) which binds to the gp130 receptor and activates a downstream pathway. LIF is a pleiotropic cytokine for which a function in pancreatic development has so far not been described. It is a well-known regulator of stem cell proliferation and differentiation and is widely used to prevent differentiation of embryonic stem cells. Truncated or mutated versions of LIF which retain the activity of binding and activating the gp130 receptor can be used as an alternative for the methods of the present invention. Equally, other naturally or modified proteins which are a ligand for gp130 and activate the downstream pathway can be used for the methods of the present invention. Examples hereof are IL-6, IL-11, OSM (oncostatin M), CNTF (Ciliary Neurotrophic Factor), G-CSF (Granulocyte-colony stimulating factor), CT-1 (cardiotrophin-1), IL-12 and Leptin.

The difference in behaviour of rodent (mouse, rat) and primate (human, monkey) cells towards LIF has been described for human ES cells and MAPC cells [Jiang et al. cited supra]. According to one embodiment human dedifferentiated pancreatic cells are incubated in a composition comprising a ligand for the EGF receptor (for example EGF) and a ligand for the gp130 receptor (for example LIF). In a specific embodiment wherein human cells are used, LIF is optional.

EGF, LIF and other compounds used in the methods of the present invention for the redifferentiation can be from the same species but can also be from another species as long as the compound can bind and activate its receptor. Thus in general the invention relates to the differentiation of cells of a first mammal by adding a ligand of the gp130 receptor pathway of a second mammal and/or a ligand of the EGF receptor pathway of a third mammal each of the first, second and third mammal are independently selected from the group of mammals, comprising but not limited to humans, primate and non primate monkeys, rodents such as hamster mouse and rat, rabbits, sheeps, cows and other cattle, dogs and porks.

In one embodiment the invention relates to the determination of properties in individual cells or in cell populations which are characteristic form mature insulin producing cells or characteristic for immature, dedifferentiated or embryonic cells. It was shown previously that exocrine acinar cells change their phenotype profoundly within only 4 days of suspension culture (Rooman et al. (2000) & (2001) cited supra). They lose amylase and other zymogens, such as pancreatic trypsinogen, trypsin and lipase, and start to express the ductal marker CK20. In Matrigel matrix they form cystic structures resembling ducts, but when they remain in suspension culture they tend to dedifferentiate and express embryonic markers like the combination of Pdx-1 and Ptf1-p48 transcription factors, the neuroendocrine marker PGP9.5, and the CCKB gastrin receptor [Rooman et al. (2000) & (2001) cited supra]. Apart from these markers, other markers for differentiated and dedifferentiated cells are known to the skilled person and can be used to evaluate the degree of differentiation of cells or cell populations.

The present invention shows that the redifferentiated cell populations or individual cells still have certain properties which are typical for undifferentiated or embryonic cells. Some of the redifferentiated cells which are insulin producing retain in the same cell properties such as the occurrence of two nuclei (binuclearity) and CK20 immunoreactivity. Thus, the present invention prevents markers and methods to distinguish between on the one hand redifferentiated cells and cell populations comprising redifferentiated cells and on the other hand mature cells and cell populations comprising mature cells.

In one embodiment of the present invention, dedifferentiated cells derived were cultured as monolayers attached to plastic, in the presence of low serum-concentration (1% FBS). Many alternative conditions can be envisaged for the cultivation of dedifferentiated cells of mammals, such as the use of suspension cultures, the use of serum of other animals apart from bovine serum, the use of alternative basis media other than RPMI-1640 and varying glucose concentrations.

The present invention includes a short-term culture model in which beta-cell neogenesis can be induced in certain animals such as rodents, especially rats by the combination of two soluble factors in the medium, namely EGF and LIF. This is the first in vitro study of acinoinsular transdifferentiation, documenting the phenotypic switch from normal exocrine to endocrine cells.

One embodiment of the invention relates to a pharmaceutical composition a population of mammalian cells comprising redifferentiated insulin secreting pancreatic cells. In addition to the cell population, the composition usually includes at least a pharmaceutically acceptable carrier, well known to those skilled in the art and for instance selected from proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregeletanized starches, pectin agar, carrageenan, days, hydrophilic gums (acacia gum, guar gum, arabic gum and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like The present invention shows the in vitro redifferentiation of dedifferentiated exocrine cells in the presence of compounds such as the combination of LIF. In alternative embodiments the redifferentiation of cells is envisaged to happen within the individual to be treated. As an example, dedifferentiated cells are embedded within a biodegradable matrix further comprising a compounds allowing a time and concentration controlled matrix comprising for example LIF and EGF, which allows the in vivo differentiation of dedifferentiated exocrine pancreatic cells. After degradation of the matrices, the differentiated cells are released. In a particular embodiment the cells are first treated with differentiating growth factors for a limited time in vitro and afterwards implanted in the presence of growth factors for further in vivo differentiation. Thus in another aspect, the invention relates to pharmaceutical composition dedifferentiated cells and compounds for the differentiation of the cells.

The following examples illustrate the present invention without being limited thereto.

EXAMPLES

Example 1

Experimental Setup

Animals: Male 10-12 week old Wistar rats (Janvier, Le Genest-St-Isle, France) weighing 250-300 g were used for the isolation of cells from the pancreas. Eight-week old male BALB/cAnNCrl-nuBR nude mice (Charles River Laboratories, Inc. Wilmington, Mass.) weighing 22-24 g were used as recipients for transplantation. All animal experimentation was approved by the Ethical Committee of the Free University of Brussels.

Isolation of exocrine tissue: Pancreata were partially dissociated with collagenase and exocrine acini were purified by centrifugal elutriation as published before (Rooman et al. (2000) & (2001) cited supra).

Culture procedure: Exocrine cells were pre-cultured for 4 days in bacteriological petri dishes (Nunc, Naperville, Ill., USA) in suspension culture in RPMI-1640 Glutamax-I medium supplemented with 10% fetal bovine serum (FBS, Gibco BRL, Paisley, Scotland), penicillin (75 mg/l) (Continental Pharma, Brussels, Belgium) and streptomycin (100 mg/l) (Sigma, St Louis, Mo., USA) and Geneticin Sulphate (50 μg/ml) (Sigma) was used to ban fibroblasts from the culture. Medium was replaced daily during this preculture period. On the fourth day after isolation cells were distributed in 1000 μl-aliquots over 24-well plates (Falcon, BD Biosciences, Erembodegem, Belgium). This procedure was standardized as to obtain approximately 75 ng DNA per well. For some experiments, the cells were treated with 10 mM alloxan for 10 minutes prior to plating. After overnight culture, nonadherent cells were washed off and then either control medium or growth factor-containing medium was added to the wells. Control medium consisted of RPMI-1640 medium supplemented with 1% FBS and antibiotics (streptomycin 0.1 g/l and penicillin 0.075 g/l). Growth factor-medium consisted of control medium supplemented with 50 ng/ml human recombinant epidermal growth factor (EGF) (Sigma, St. Louis, Mo.) and 40 ng/ml recombinant mouse leukemia inhibitory factor (LIF) (Sigma). Cell monolayers were analysed after a culture period of 3 days in the latter media.

Immunocytochemistry and DNA measurement: The amount of cells per well was measured by a DNA fluorimetric assay based on the binding of Hoechst 33258 dye [Loontiens et al. in *Biochemistry*. (1990) 29, 9029-9039]. At least 6 wells were used per experimental condition, so that triplicate cultures could be used for DNA-extraction and, in parallel, for immunocytochemical analysis of cell composition. Immunocytochemical staining of the monolayers was performed directly in the 24-well plates. For this purpose, the cell monolayers were fixed for 10 min with 4% buffered formaldehyde followed by 20 min methanol (−20° C.) for cell permeabilization. For single stainings of only one antigen, the streptavidin-biotin peroxidase method was used [Bouwens et al. in *Diabetes*. (1994) 43, 1279-1283; Bouwens & De Blay in *J Histochem Cytochem*. (1996) 44, 947-951]. For double staining, the indirect method with FITC- and TRITC-labeled secondary antibodies was used (Jackson Immunoresearch, West Grove, Pa.). Primary antibodies used in this study are polyclonal anti-insulin (C. Van Schravendijk, VUB, Brussels) [Bouwens et al. (1994) cited supra; Bouwens & De Blay cited supra], polyclonal anti-rat C-peptide-I (O.D. Madsen, Hagedorn Research Institute, Gentofte, Denmark [Blume et al. in *Mol Endocrinol*. (1992) 6, 299-307], polyclonal anti-Pdx1 (O.D. Madsen) [Rooman et al. (2000) cited supra], polyclonal anti-Glut-2 (Wak-Chemie, Bad Soden, Germany), monoclonal anti-cytokeratin-20 (CK20) (Novocastra, Newcastle-upon-Tyne, UK)( Bouwens et al. (1994) cited supra; Bouwens & De Blay cited supra), polyclonal anti-alpha-amylase (Sigma), and mouse monoclonal anti-BrdU (ICN, Irvine, Calif., USA). To assess the incorporation of 5'-bromodeoxyuridine (BrdU) by proliferating cells, 10 μM BrdU (Sigma) was added to the culture medium one hour before fixation (Rooman et al. (2001) cited supra). For BrdU pulse-chase labeling, BrdU was added to the culture medium on the first day of adherent cell culture and removed 24 h later. The cells were analyzed 24 h after the pulse or on day 3 of cell culture, i.e. after 48 h chasing in the absence of BrdU. BrdU incorporation was scored both in insulin-expressing cells and in cytokeratin-expressing cells.

RT-PCR analyses: Total RNA was extracted from monolayer cell culture of rat pancreatic cells using Trizol RNA isolation method (Invitrogen Life Technologies, Carlsbad, Calif.). For the semi-quantitative analysis of transcripts encoding notch-1 and glyceraldehyde phosphate dehydrogenase, the total RNA was reversed transcribed and amplified as described by the manufacturer (Invitrogen Life Technologies). PCR products were separated by electrophoresis in 1.5-2.5% agarose gels and visualized by ethidium bromide staining. Analyses were performed at least three times.

Morphometry: Computer-assisted morphometry [Bouwens et al. (1994) cited above] was used to measure the area of monolayers in 24-well plates.

Insulin measurements: Cellular insulin content and insulin released in the medium were measured by radio-immunoassay [Pipeleers et al. cited supra]. To study glucose-stimulated insulin release, insulin in the culture medium was measured after a 4 hour incubation in basal medium containing 2.5 mM glucose, followed by a 4 hour incubation in 20 mM glucose (serum-and glutamine-free HAM-10 medium, Gibco) [Lobner et al. in *Diabetes* (2002) 51, 2982-2988].

Transplantation: To transplant the monolayer cells, they were cultured on collagen S from calf skin (type I; Roche Molecular Biochemicals, Mannheim, Germany) and detached with collagenase P (Roche Molecular Biochemicals). Cell pellets were implanted under the kidney capsule (17) of nude mice that had been injected intravenously with 70 mg/kg alloxan 3 hours prior to transplantation. Blood glucose levels were monitored every two days in samples obtained from the tail vein of fed mice by using Glucocard Memory strips (A. Menarini Diagnostics Benelux, Zaventem, Belgium).

Statistics: A two-tailed, paired Student t-test was used and statistical significance was considered at a confidence interval <0.05. Mean values are given ±SEM. Repeats of independent experiments are indicated as n=x (x being the number of repeats) with each cell preparation being a pool from a total of 5 rats.

Example 2

Generation and Composition of Exocrine Cell Monolayers

Isolated and pre-cultured exocrine acinar cell aggregates were obtained as described earlier (Rooman et al. (2000) & (2001) cited supra) and subsequently allowed these cells to form monolayers on plastic. More than 90% of the cells were immunoreactive for the ductal marker CK20 and had lost the amylase marker of acinar cells. (Of these cells, 79.0±0.4% (n=7) were binucleated, a characteristic of part of the acinar cells. These cultures were initially contaminated with 3.7±0.46% (n=7) insulin-positive cells. When the cell preparations had been pre-treated with alloxan prior to monolayer formation, the monolayers contained less than 0.5% insulin-positive cells. When geniticine was used during the cultivation, the outgrowth of fibriblastic cells was inhibited.

Published data showed that exocrine acinar cells lose their differentiated characteristics like amylase and other zymogens within 4 days of suspension culture and start to express ductal and embryonic characteristics like CK20, the combination of Pdx-1 and Ptf1-p48 transcription factors, the neuroendocrine markers PGP9.5 and the CCKB gastrin receptor (Rooman et al. (2000) & (2001) cited supra; Lardon et al. (2004) *Virchows Arch.* 444, 61-65). In the presence of dexamethasone, it was shown that these cells can transdifferentiate into hepatocyte-like cells [Lardon et al. (2004) in *Hepatology* 39, 1499-1507]. For the present study these cells were cultured as monolayers attached to plastic, in the presence of low serum-concentration (1% FBS) and were tested for the effect of the combination of LIF and EGF. These factors are known to control the differentiation of adult and embryonic neural stem cells (Viti et al. (2003) in *J. Neurosci.* 15, 3385-3393).

Example 3

Effect of Growth Factors on Cell Number and Beta-Cell Frequency

Figure 1:
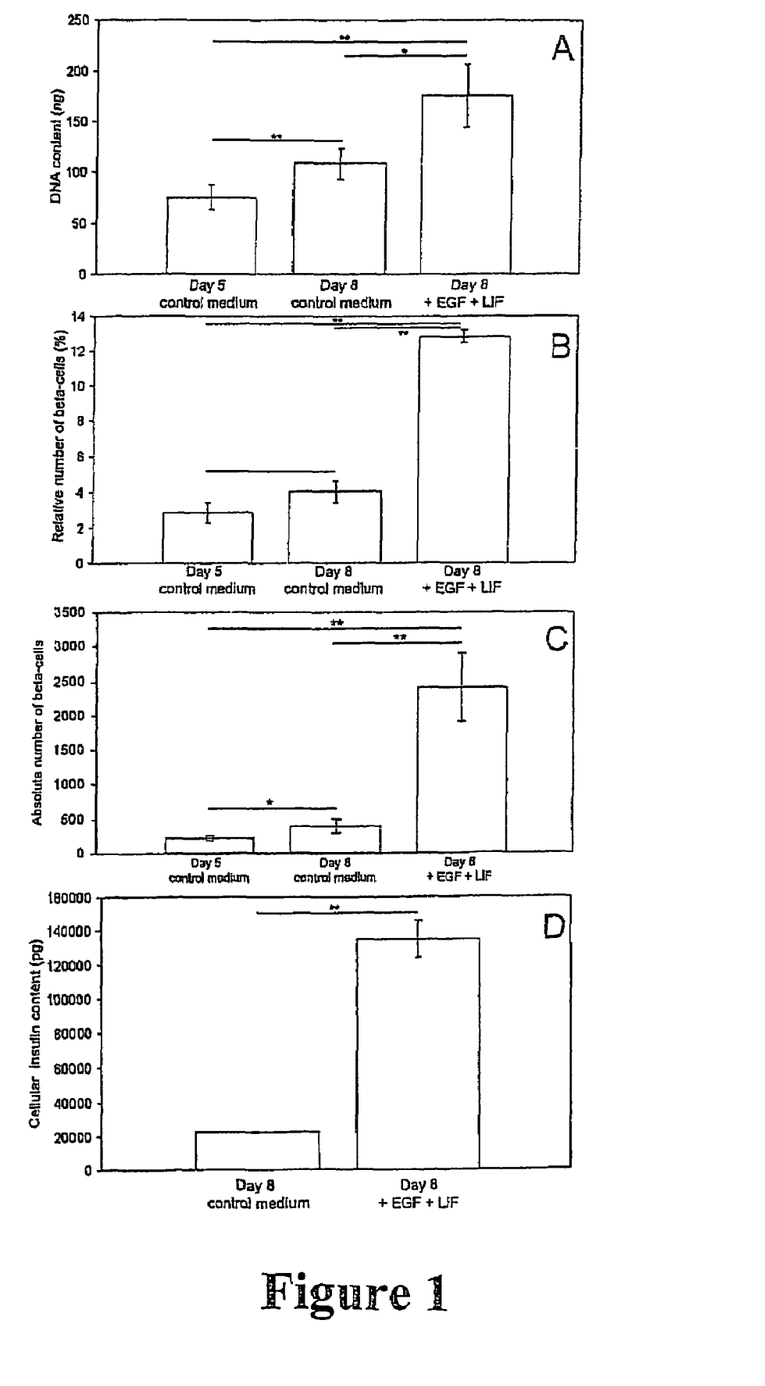
FIG. 1 shows, according to an embodiment of the invention, an increase in DNA (A), % insulin-positive cells (B), beta-cell number (C), cellular insulin content (D) of cultures grown in the presence of EGF and LIF compared to cultures without these growth factors (*=p<0.05; **=p<0.01). Cells are kept for 5 days in the medium (left) prior to a three day period without (middle) or with EGF+LIF (right).

When monolayer cultures were treated with LIF and EGF for 3 days, a significant increase in DNA content was noted compared to the start of the culture and compared to cultures devoid of both growth factors (FIG. 1A). The total surface covered with cells which was measured by morphometry showed a comparable increase.

Treatment with LIF and EGF also induced a significant increase in the frequency of insulin-positive cells, expressed as the percentage of all cells (FIG. 1B). When multiplying the frequency of insulin-positive cells with total DNA-content to have a measure of the absolute beta-cell number, an 11-fold increase in beta-cell number was observed in the presence of LIF and EGF over the 3-day culture period (FIG. 1C). Analysis of total cellular insulin content by radio-immunoassay showed a 6-fold increase in LIF and EGF treated cultures compared to control cultures (FIG. 1D).

In the presence of either LIF or EGF alone there was also a significant increase in beta-cell number, respectively 6- and 5-fold compared to the start material, but these increases were significantly lower than in the presence of both factors together.

In alloxan pre-treated cultures depleted of contaminating beta-cells, and after 3 days of culture in the presence of LIF and EGF, 9.2±1.5% insulin-positive cells were found (n=4). In the absence of growth factors there were 0.4±0.1% insulin-positive cells. The upregulation of insulin-positive cells which was seen with the combination of both factors, was not observed when either EGF or LIF was given alone.

The cells populations which are obtained according to the methods of the present invention can be further enriched for insulin secreting cells by methods such as FACS sorting, size fractionation and elutriation as explained in e.g. EP1146117.

In vitro, EGF or LIF alone also had an effect on the number of beta cells. This can be explained by the observation that these factors are also produced by the cultured cells and can work in a paracrine or autocrine manner (unpublished observations). In the present invention it was shown that LIF is produced by beta cells, thus suggesting that beta cells can stimulate their own regeneration from the precursor cells. Beta cells also produce other factors which can regulate islet neogenesis, for example netrin [De Breuck et al. in *Diabetologia* (2003) 46, 926-933] and vascular endothelial growth factor [Rooman et al. in *Lab Invest.* 76, 225-232]. These observations may explain why "spontaneous" islet regeneration following toxic or autoimmune insult is limited.

In the present model of dedifferentiated exocrine cells, the combination of LIF and EGF was found to stimulate cell proliferation as evidenced by a significant increase in total DNA and a larger area occupied by the monolayers. The combination of LIF and EGF also resulted in an approximate sixfold increase in the percentage of insulin-positive cells.

Combined with the observed increase in DNA, this gives more than a tenfold increase in number of insulin-containing cells.

Example 4

Phenotypic Analysis

Analysis by double immunofluorescence staining showed that most of these insulin-positive cells also expressed other beta-cell markers, including proinsulin C-peptide-I, the transcription factor Pdx-1, and the glucose transporter Glut-2. Immunoreactivity for C-peptide excludes the possibility of insulin uptake from the medium as an explanation for the increased frequency of insulin-immunoreactive cells (insulin was not added to the medium).

In the EGF+LIF-treated cultures, approximately 10% of the insulin-positive cells were immunoreactive for CK20, with a somewhat lower staining intensity compared to insulin-negative cells. Co-expression of insulin and CK20 was rarely observed in control cultures where no growth factors were added and it was not seen in the starting material. This co-expression suggests a phenotypic transition from exocrine to insulin-positive cells. Strikingly, insulin and CK20-double-positive cells were observed that were binuclear. Binuclear insulin-positive cells were rarely seen in control cultures and were absent at the start, but they were frequently seen in EGF+LIF-treated cultures where they accounted for 6.2±0.47% (n=7) of all insulin-positive cells. In exocrine cell-derived monolayers of the present invention, nearly 80% of the cells were binuclear. Since binuclearity is a characteristic of the majority of acinar exocrine cells [Ramiya et al. cited supra], these observations are another indication for a transition from exocrine cells to insulin-positive cells. The redifferentiated cells which were obtained using the method of the present invention have the striking characteristic that the population as a whole, but also some individual cells still retain both the features of fully differentiated cells but also of incompletely differentiated embryonic or adult precursor cells. These features are exemplified in this and the following examples. This property of harbouring both markers of differentiated and undifferentiated cells allows the distinction between cells obtained by the present method and freshly isolated cells from a pancreas, especially from a pancreas of an adult.

The majority of these insulin-containing cells could be considered as mature beta-cells since they expressed other phenotypic characteristics of beta-cells, such as the insulin-transactivating transcription factor Pdx-1, the beta-cell specific glucose transporter Glut-2, and the C-peptide-I component of unprocessed proinsulin. There were very few BrdU-labeled beta-cells so that the observed increase in their number within a period of 3 days must be attributed to the differentiation of precursor cells, or neogenesis.

There were two indications that the exocrine cells served as precursor cells of the newly formed beta-cells. First, CK20 immunoreactivity was noted in part of the insulin-positive cells. It was shown before that beta-cells containing CK20 are only found in the fetal [Bouwens & DeBlay, cited supra] and neonatal pancreas [Bouwens et al. (1994), cited supra], and in adult pancreas when neogenesis has been induced by duct-ligation [Wang et al. cited supra]. Thus, CK20 expression is a good indication for a transition from the CK20-positive exocrine cells to beta-cells. Second, binuclearity was noted in part of the insulin-positive cells. Binuclearity is a characteristic of acinar exocrine cells, and is not observed in normal rat beta-cells [Rooman et al.(2000) cited supra]. This is another indication for a transition from the exocrine cells to beta-cells. It is unlikely that binuclear beta-cells would represent dividing cells blocked before cytokinesis since there was very little beta-cell mitotic activity (BrdU-incorporation). Cell fusion between beta-cells can not be completely excluded although this would rather lead to a decrease in beta-cell number instead of the observed increase. Unpublished observations with mitomycin-c and cytochalasin-B predict that insulin-positive cells could also arise from binucleated (exocrine) cells by a kind of delayed cytokinesis or cleavage process. Somatic cell cleavage or reduction-division has been demonstrated indirectly from tetraploid hybrid cells but the mechanism has not yet been characterized [Wang et al. in *Nature* (2003) 422, 897-901].

Example 5

Proliferation

Analysis of BrdU-incorporation in insulin-positive cells showed that less than 0.1% of insulin-positive cells were BrdU-labelled after a pulse of one hour. This makes it highly unlikely that binuclearity in these cells would have resulted from arrested nuclear division in mitotic beta-cells, or that the increase in beta-cell number would have resulted from proliferation of contaminating beta-cells. Approximately 1.5% of the exocrine cells were BrdU-labeled.

Figure 2:
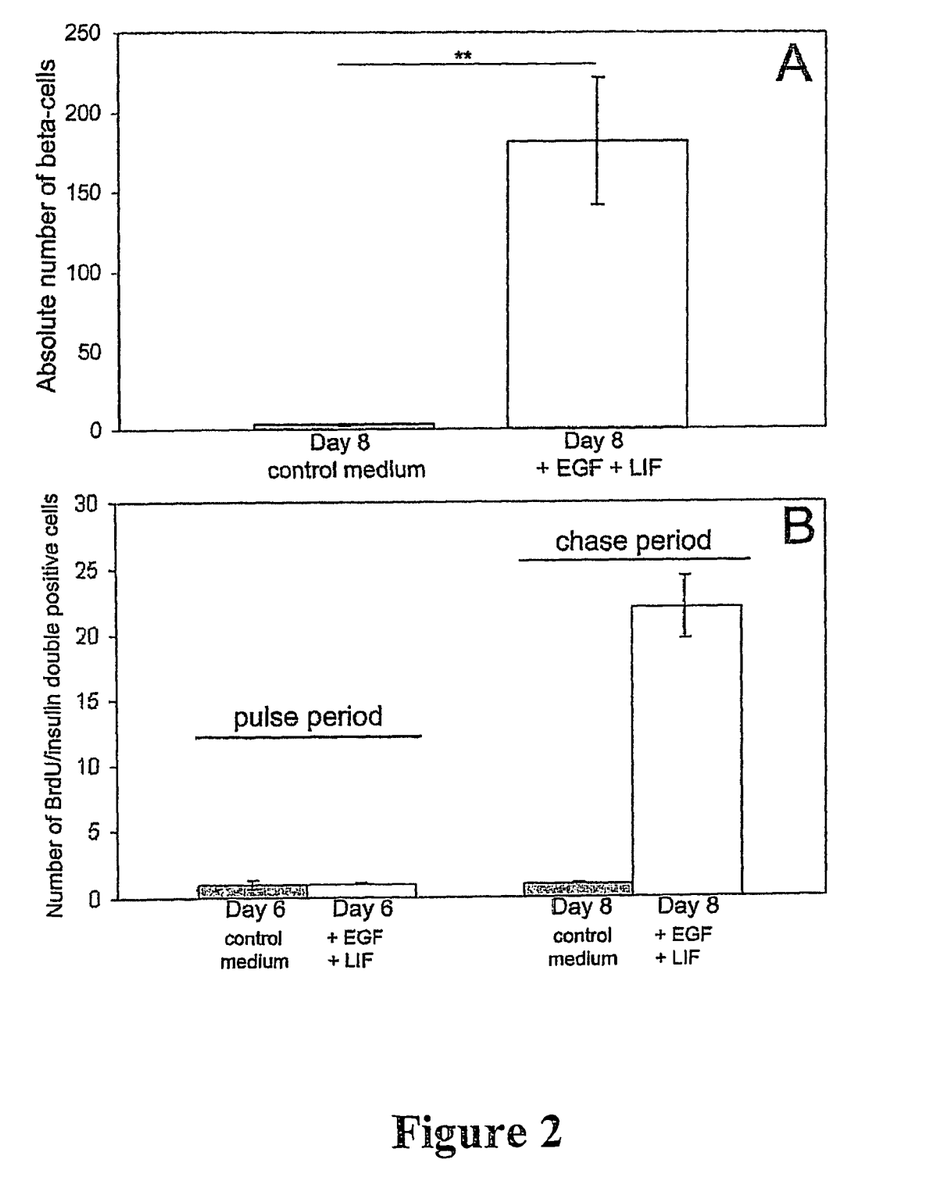
FIG. 2 shows, according to an embodiment of the invention, the increase of insulin-positive beta cells in control medium versus with both EGF and LIF treated cultures, after pretreatment with alloxan (A) (n=4), number of BrdU-labeled insulin positive beta-cells in the presence of EGF and LIF during the pulse and the chase period (B) (n=4). (**=p<0.01).

A BrdU pulse-chase experiment over a 72-hour period (a pulse period of 24 hours and a chase of 48 hours) revealed a significant increase in BrdU-labeled beta-cells in the presence of EGF and LIF during the chase period (FIG. 2B). This increase can only be explained by the differentiation of proliferating exocrine cells into non-proliferating beta-cells.

Data with mitomycin-C (inhibitor of proliferation) and cytochalasin-B (inhibitor of cytokinesis) indicate that binucleated cells were able to divide into mononucleated cells (expressing insulin) without going through the cell cycle, suggesting the existence of a kind of delayed cytokinesis or cleavage phenomenon.

Example 6

PCR Analysis of Mature and Embryonic Markers

RT-PCR analysis revealed that Notch expression was absent in the monolayers cultured in control-medium (day 8) and that Notch was upregulated in the monolayers in the presence of EGF and LIF. Notch is absent in rat islets.

Example 7

Insulin Secretion

Insulin secretion studies were done over 4 h in the above mentioned cell culture conditions. Compared to their basal secretion in 2.5 mM glucose, stimulation by 20 mM glucose gave a 4-fold increase in secreted insulin, namely from 2.3 to 9.5 ng/ml.

Example 8

Transplantation

Figure 3:
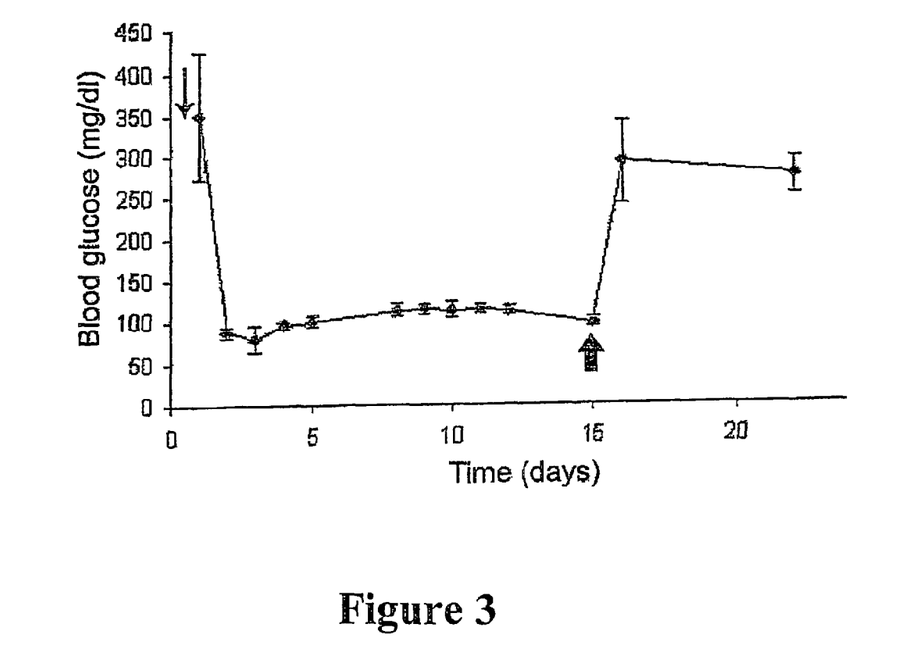
FIG. 3 shows, according to an embodiment of the invention, an in vivo diabetic mouse model using EGF+LIF redifferentiated cells of the present invention.

Detached monolayers of dedifferentiated pancretic rat cells treated with LIF and EGF were transplanted and observed into alloxan-treated nude mice. Mice treated with 70 mg/kg alloxan remain permanently hyperglycemic or die within one week [Wang et al. in *Diabetologia*. (1995) 38, 1405-1411]. Engraftment resulted in normalization of blood glycemia which was retained over a 14 day period but promptly reverted to hyperglycemia when the graft-bearing kidney was removed (FIG. 3). This demonstrates that the redifferentiated beta cells obtained in vitro with LIF and EGF, in accordance with the present invention are able to control blood glycemia in vivo.

The invention claimed is:

1. An In vitro method of generating insulin producing beta cells from a population comprising dedifferentiated exocrine pancreatic cells of a first mammal, said method comprising the steps of:
   a) providing a population comprising dedifferentiated exocrine pancreatic cells in a culture medium,
   b) adding one or more ligands of the gp130 receptor of a second mammal and adding one or more ligands of the EGF receptor of a third mammal to said culture medium,
   c) incubating said dedifferentiated exocrine pancreatic cells in said culture medium comprising said one or more ligands of the gp130 receptor and said one or more ligands of the EGF receptor,
wherein one of said one or more ligands of the EGF receptor is EGF.

2. The method according to claim 1, wherein said ligand of said gp130 receptor is LIF.

3. The method according to claim 1, wherein the method further comprises the step of adding bFGF to said culture medium during step b).

4. The method according to claim 1, wherein said medium is free from KGF or a gastrin/CCK receptor ligand.

5. The method according to claim 1, wherein the population comprising dedifferentiated exocrine pancreatic cells is selected from the group consisting of duct cells, acinar cells and islet cells.

6. The method according to claim 1, further comprising, prior to step a), a preliminary step of depleting beta cells from said population.

7. A population of mammalian pancreatic cells comprising mammalian insulin producing beta cells obtainable by an in vitro method of generating insulin producing beta cells from a population comprising dedifferentiated exocrine pancreatic cells of a first mammal, said method comprising the steps of:
   a) providing a population comprising dedifferentiated exocrine pancreatic cells in a culture medium,
   b) adding one or more ligands of the gp130 receptor of a second mammal and adding one or more ligands of the EGF receptor of a third mammal to said culture medium,
   c) incubating said dedifferentiated exocrine pancreatic cells in said culture medium comprising said one or more ligands of the gp130 receptor and said one or more ligands of the EGF receptor,
wherein one of said one or more ligands of the EGF receptor is EGF.

8. The population of mammalian pancreatic cells according to claim 7, wherein said population comprises from about 5 to about 15 percent of insulin- positive cells.

9. The population of mammalian pancreatic cells according to claim 7, wherein said cell population after exposure to 20 mM glucose for 4 hours at 37° C. in RPMI-1640 medium supplemented with 10% fetal bovine serum shows a more than 2 fold increase in insulin secretion when compared to the insulin secretion prior to said exposure to glucose.

10. A pharmaceutical composition comprising a therapeutically active amount of a mammalian pancreatic cell population according to claim 7, and at least one pharmaceutically acceptable carrier.

11. An In vitro method for determining the degree of redifferentiation of the population of mammalian pancreatic cells according to claim 7 comprising the steps of determining one or more parameters selected from the group consisting of:
   a) the presence of CK 20, CK7 or CK 19,
   b) the occurrence of binucleated cells,
   c) the presence of insulin positive cells,
   d) the presence of C-peptide, Pdx-i and Glut-2,
   e) the presence of gastrin CCKB receptor, PGP9.5 and notch-1 receptor, on said mammalian pancreatic cells.

12. The method according to claim 1, wherein said cells are grown on a surface which is a plastic surface.

* * * * *

UNITED STATES PATENT AND TRADEMARK OFFICE
CERTIFICATE OF CORRECTION

PATENT NO.        : 7,604,991 B2                                              Page 1 of 1
APPLICATION NO. : 10/561449
DATED             : October 20, 2009
INVENTOR(S)       : Bouwens et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 431 days.

Signed and Sealed this

Fifth Day of October, 2010

David J. Kappos
*Director of the United States Patent and Trademark Office*